(12) United States Patent
DeVaux

(10) Patent No.: US 7,674,252 B2
(45) Date of Patent: Mar. 9, 2010

(54) SINGLE OPERATOR SHEATH CATHETER

(75) Inventor: Barbara DeVaux, Haverhill, MA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 260 days.

(21) Appl. No.: 11/197,274

(22) Filed: Aug. 4, 2005

(65) Prior Publication Data

US 2007/0032815 A1 Feb. 8, 2007

(51) Int. Cl.
A61M 25/00 (2006.01)
A61M 29/00 (2006.01)

(52) U.S. Cl. .................. 604/526; 606/200; 604/524

(58) Field of Classification Search ........... 606/200; 604/103.04, 103.05, 103.09, 524, 526, 527
See application file for complete search history.

(56) References Cited

U.S. PATENT DOCUMENTS

| 4,748,982 | A |   | 6/1988  | Horzewski et al. |
|-----------|---|---|---------|------------------|
| 4,994,069 | A | * | 2/1991  | Ritchart et al. ............... 606/191 |
| 5,156,594 | A |   | 10/1992 | Keith            |
| 5,234,437 | A | * | 8/1993  | Sepetka ....................... 606/108 |
| 5,290,247 | A |   | 3/1994  | Crittenden       |
| 6,059,770 | A | * | 5/2000  | Peacock et al. .............. 604/526 |
| 6,193,686 | B1| * | 2/2001  | Estrada et al. .......... 604/103.09 |
| 6,203,547 | B1| * | 3/2001  | Nguyen et al. .............. 606/102 |
| 6,620,149 | B1|   | 9/2003  | Lenz et al.      |
| 6,932,830 | B2| * | 8/2005  | Ungs .......................... 606/200 |
| 2002/0016597 | A1 | | 2/2002 | Dwyer et al. |
| 2002/0095141 | A1 | | 7/2002 | Belef et al. |
| 2003/0004537 | A1 | | 1/2003 | Boyle et al. |
| 2003/0093110 | A1 | | 5/2003 | Vale |
| 2003/0125751 | A1 | | 7/2003 | Griffin et al. |

FOREIGN PATENT DOCUMENTS

WO WO03/094789 11/2003

* cited by examiner

Primary Examiner—(Jackie) Tan-Uyen T. Ho
Assistant Examiner—Melissa Ryckman

(57) ABSTRACT

A sheath catheter used to compress and/or retrieve a filter from a body lumen. The sheath catheter includes an elongate proximal shaft and a distal recovery sheath. The proximal shaft includes a central lumen that accommodates a shaft portion of a solid core wire to provide the catheter with better pushability. The solid core wire further includes a coiled portion that extends within the recovery sheath from a distal end of the proximal shaft. The coiled portion of the core wire provides a transition in flexibility from the stiffer proximal shaft to the more flexible recovery sheath. The recovery sheath further includes a sheath lumen that is sized to receive the filter therein.

20 Claims, 3 Drawing Sheets

SINGLE OPERATOR SHEATH CATHETER

FIELD OF THE INVENTION

The invention relates to catheters for use within a body lumen of a patient, and more particularly to sheath catheters for use in deploying and retrieving therapeutic or interventional medical devices.

BACKGROUND OF THE INVENTION

Catheters have long been used for the treatment of diseases of the cardiovascular system, such as treatment or removal of stenosis. For example, in a percutaneous transluminal coronary angioplasty (PTCA) procedure, a catheter is used to insert a balloon into a patient's cardiovascular system, position the balloon at a desired treatment location, inflate the balloon, and remove the balloon from the patient. Another example is the placement of a prosthetic stent that is placed in the body on a permanent or semi-permanent basis to support weakened or diseased vascular walls to avoid closure or rupture thereof.

These non-surgical interventional procedures often avoid the necessity of major surgical operations. However, one common problem associated with these procedures is the potential release of embolic debris into the bloodstream that can occlude distal vasculature and cause significant health problems to the patient. For example, during deployment of a stent, it is possible for the metal struts of the stent to cut into the stenosis and shear off pieces of plaque which become embolic debris that can travel downstream and lodge somewhere in the patient's vascular system. Further, pieces of plaque material can sometimes dislodge from the stenosis during a balloon angioplasty procedure and become released into the bloodstream.

Medical devices have been developed to attempt to deal with the problem created when debris or fragments enter the circulatory system during vessel treatment. One technique includes the placement of a filter or trap downstream from the treatment site to capture embolic debris before it reaches the smaller blood vessels downstream. The placement of a filter in the patient's vasculature during treatment of the vascular lesion can collect embolic debris in the bloodstream.

It is known to attach an expandable filter to a distal end of a guidewire or guidewire-like member that allows the filtering device to be placed in the patient's vasculature. The guidewire allows the physician to steer the filter to a downstream location from the area of treatment. Once the guidewire is in proper position in the vasculature, the embolic filter can be deployed to capture embolic debris. Some embolic filtering devices utilize a restraining sheath to maintain the expandable filter in its collapsed configuration. Once the proximal end of the restraining sheath is retracted by the physician, the expandable filter will transform into its fully expanded configuration. The restraining sheath can then be removed from the guidewire allowing the guidewire to be used by the physician to deliver interventional devices, such as a balloon angioplasty catheter or a stent delivery catheter, into the area of treatment. After the interventional procedure is completed, a recovery sheath can be delivered over the guidewire using over-the-wire techniques to collapse the expanded filter (with the trapped embolic debris) for removal from the patient's vasculature. Both the delivery sheath and recovery sheath should be relatively flexible to track over the guide wire and to avoid straightening the body vessel once in place.

Another distal protection device known in the art includes a filter mounted on a distal portion of a hollow guidewire or tube. A moveable core wire is used to open and close the filter. The filter is coupled at a proximal end to the tube and at a distal end to the core wire. Pulling on the core wire while pushing on the tube draws the ends of the filter toward each other, causing the filter framework between the ends to expand outward into contact with the vessel wall. Filter mesh material is mounted to the filter framework. To collapse the filter, the procedure is reversed, i.e., pulling the tube proximally while pushing the core wire distally to force the filter ends apart. A sheath catheter may be used as a retrieval catheter at the end of the interventional procedure to reduce the profile of the "push-pull" filter, as due to the embolic particles collected, the filter may still be in a somewhat expanded state. The retrieval catheter may be used to further collapse the filter and smooth the profile thereof, so that the filter guidewire may pass through the treatment area without disturbing any stents or otherwise interfering with the treated vessel.

Sheath catheters may be of the "over-the-wire" variety with a guidewire lumen extending the entire length of the catheter, such that the guidewire is disposed entirely within the catheter except for the distal and proximal portions of the guidewire that protrude from the catheter. While these catheters are advantageous in many ways, exchanging the indwelling sheath catheter for another interventional or the retrieval catheter can be difficult often requiring multiple operators and the use of an exchange wire.

Sheath catheters may also be of the single operator or "rapid-exchange" type. A rapid-exchange sheath catheter typically includes a tubular body with a lumen extending the entire length thereof and a guidewire shaft having a guidewire lumen of minimal length positioned along a distal portion of the catheter, although some of these catheters are not advanced over guidewires at all. As such, the guidewire is located outside of the sheath catheter except for a short segment which runs within the guidewire lumen. As such, a clinician is able to control both ends of the guidewire while the sheath catheter is loaded onto the guidewire. The sheath catheter is then advanced through the patient with only a distal portion of the catheter "riding" on the guidewire.

While convenient for rapid and simple exchange, a rapid-exchange type sheath catheter sometimes lacks the desired stiffness and pushability for readily advancing the sheath catheter through the tortuous vascular system.

What is needed is a reliable sheath catheter that can be used with embolic filtering devices. The sheath catheter should be relatively easy for a physician to use and should provide an effective means for retrieving the filtering device without releasing any captured embolic debris into the body vessel. Moreover, the sheath catheter should be advance-able and removable from the guidewire in relatively quick fashion.

BRIEF SUMMARY OF THE INVENTION

Accordingly disclosed herein in one embodiment is a filter recovery catheter having an elongate proximal shaft and a distal recovery sheath. The proximal shaft includes a central lumen that accommodates a shaft portion of a solid core wire to provide the catheter with better pushability. The solid core wire further includes a coiled portion that extends within the recovery sheath from a distal end of the proximal shaft. The coiled portion of the core wire provides a transition in flexibility from the stiffer proximal shaft to the more flexible recovery sheath to prevent kinking of the catheter at this juncture. The recovery sheath further includes a sheath lumen that is sized to receive an embolic filter therein.

In another embodiment, a sheath catheter is disclosed having an elongate proximal shaft and a sheath. The proximal shaft includes a hypotube having a central lumen for receiving a solid core wire. The solid core wire further includes a coiled portion that extends within the sheath from a distal end of the hypotube. The sheath further includes a guidewire port for accessing a sheath lumen.

BRIEF DESCRIPTION OF DRAWINGS

The foregoing and other features and advantages of the invention will be apparent from the following description of the invention as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments of the present invention are now described with reference to the figures, where like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

Figure 1:
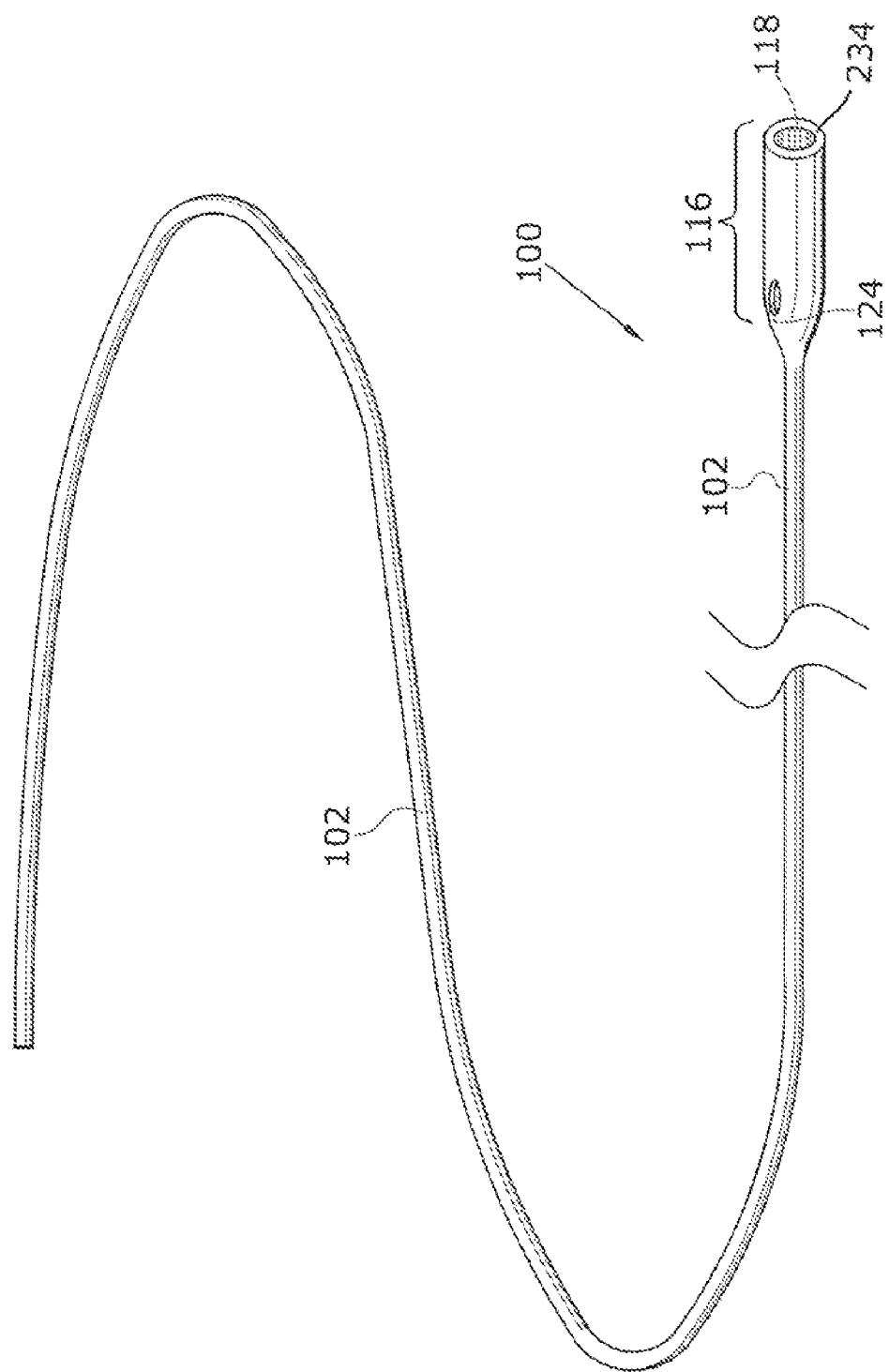
FIG. 1 is a perspective view of a sheath catheter in accordance with an embodiment of the present invention.
Figure 1A:
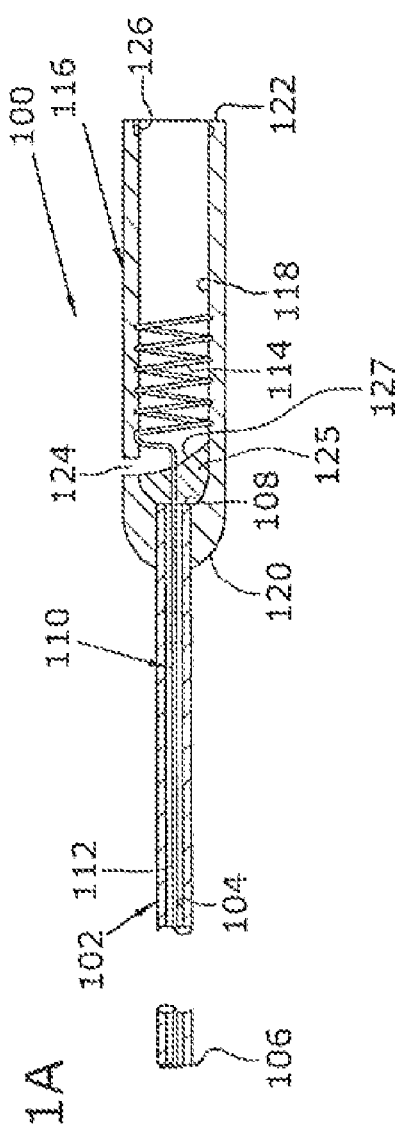
FIG. 1A is a sectional view of a portion of the catheter of FIG. 1.
Figure 1B:
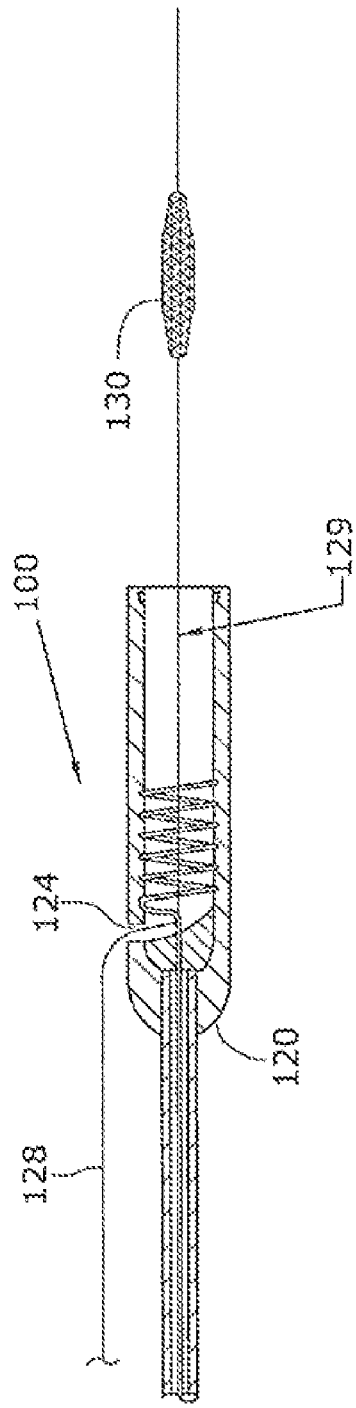
FIG. 1B is a sectional view of the portion of the catheter of FIG. 1A with a filter guidewire extending therethrough.

FIGS. 1, 1A and 1B illustrate a sheath catheter 100 according to an embodiment of the present invention, which may be utilized in the delivery and/or recovery of an embolic filter. Sheath catheter 100 includes an elongate proximal shaft 102 having a central lumen 104 that extends from a proximal end 106 to a distal end 108 thereof. In one embodiment, proximal shaft 102 includes a thin-walled, tubular structure of a metallic material, such as stainless steel or nitinol. Such a metallic tube is commonly referred to as hypodermic tubing or a hypotube. In an alternate embodiment, proximal shaft 102 includes a tube structure made from a polymeric material, such as polyethylene block amide copolymer, polyvinyl chloride, polyethylene, polyethylene terephthalate, polyamide, or polyimide.

Proximal shaft 102 must be flexible enough to navigate the tortuous pathways of the vascular system and yet have pushability. To impart improved pushability to sheath catheter 100, a shaft portion 112 of a solid core wire 110 extends within central lumen 104 of proximal shaft 102. Core wire 110 is formed from a material such as stainless steel or a nickel-based super alloy. In FIG. 1A, core wire 110 further includes a coiled portion 114 with windings that extend from distal end 108 of proximal shaft 102. In an embodiment, core wire 110 may have to be ground down and have several diameters in its profile in order to provide stiffness transition and the ability to be coiled. In another embodiment, coiled portion 114 may be a separate component from core wire 110 that is formed from a round or flat coil of stainless steel.

As illustrated in FIG. 1A, a sheath 116 having a sheath lumen 118 is attached proximate to distal end 108 of proximal shaft 102. In one embodiment, sheath lumen 118 is sized for aiding in the compression and/or retrieval of a filter guidewire, such as any of the filter guidewires disclosed in U.S. Pat. No. 6,706,055, U.S. Pat. No. 6,818,006 and U.S. Pat. No. 6,866,677, which are incorporated by reference herein in their entireties. Sheath 116 is preferably made from a flexible, low-expansive material that provides column strength and some axial stiffness. Examples of suitable polymeric materials include polyethylene block amide copolymer, high density polyethylene (HDPE), polyolefin, and polyamide. A distal end 122 of sheath 116 includes a radiopaque marker band 126 embedded therein as a fluoroscopic aid in placement of the sheath within a body lumen.

Figure 3:
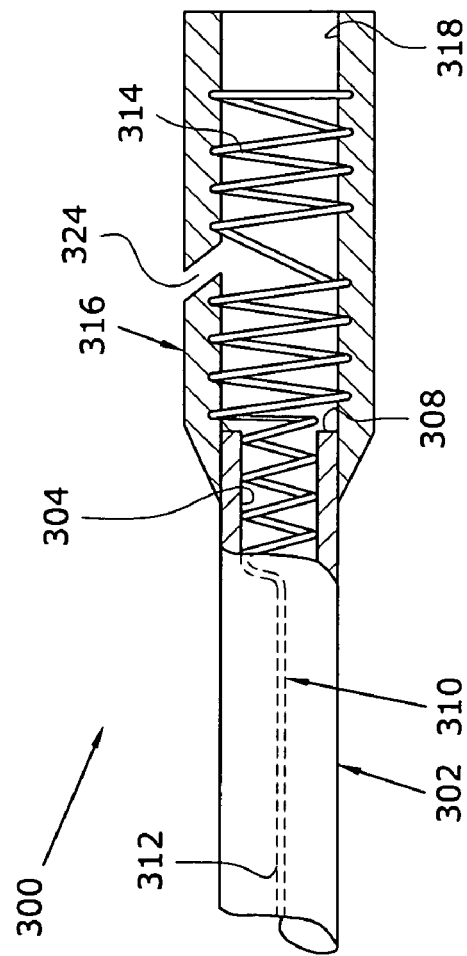
FIG. 3 is a partial sectional view of another embodiment of the present invention.

A proximal portion of sheath lumen 118 surrounds the windings of core wire coiled portion 114. Coiled portion 114 provides a transition in flexibility between the stiffer proximal shaft 102 and the more flexible sheath 116 to prevent kinking of sheath catheter 100 at this juncture. The windings of coiled portion 114 may be uniformly or variably spaced depending on the desired transition in flexibility. In one embodiment, core wire 110 is tapered in coiled portion 114. In another embodiment as illustrated in FIG. 3, the windings of a core wire coiled portion 314 are at least partially embedded in a wall of a sheath 316.

In a still further embodiment of the present invention, the windings of the core wire coiled portion may be fully encased within the sheath wall. In order to fully encase the coiled portion within the sheath wall, the coiled portion may be encased between laminated layers of the sheath or may be embedded into the sheath wall through the use of a shrink-tubing formation process, as would be known to one of ordinary skill in the art.

In FIG. 1B, sheath catheter 100 is illustrated being tracked over a filter guidewire 129 comprised of a guidewire 128 and an embolic filter 130. Guidewire 128 traverses a guidewire exit 124, which is disposed through a side wall of sheath 116 adjacent to a proximal end 120 of sheath 116, as sheath catheter 100 is advanced or retracted from a body lumen. In an embodiment of the present invention, a plug 125 with a ramp portion 127 may be formed within sheath lumen 118 proximal of guidewire exit 124 by a method disclosed in U.S. Pat. No. 4,748,982, which is incorporated by reference herein in its entirety, or by any other method known to one of ordinary skill in the art. Ramp portion 127 eases the clinician's insertion of a proximal end of guidewire 128 through guidewire exit 124 during backloading of the sheath catheter onto the guidewire. In another embodiment, a short guidewire tube (not shown) having at least a distal portion with an outer diameter that is formed to be substantially equal to a diameter of sheath lumen 118, 218 or 318 may be positioned and secured between guidewire exit 124, 224 or 324 and a point distal thereof. In this configuration, the proximal end of guidewire 128 is guided through the guidewire tube to traverse guidewire exit 124 during backloading of the sheath catheter onto the guidewire.

Figure 2:
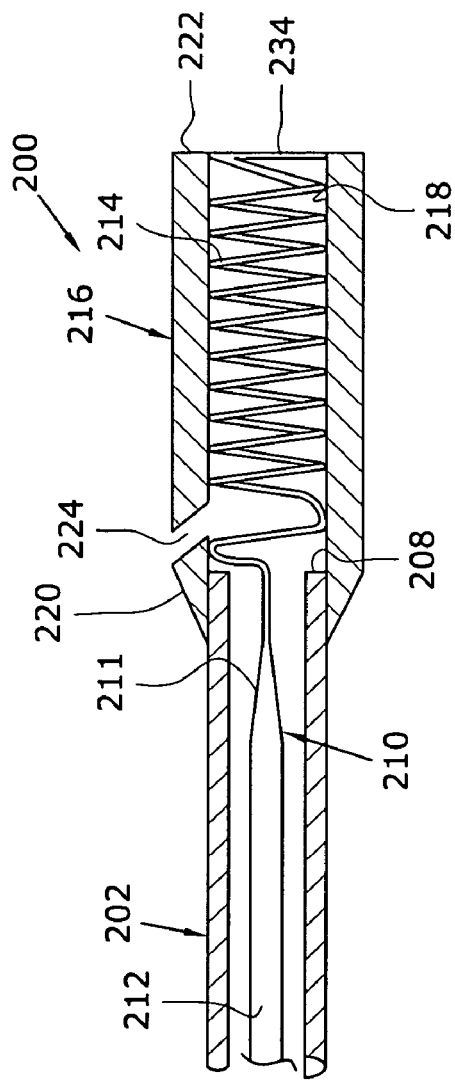
FIG. 2 is a sectional view of another embodiment of the present invention.

In FIG. 2, a sheath catheter 200 is illustrated in accordance with another embodiment of the present invention. Sheath catheter 200 includes a core wire 210 having a coiled portion 214 that extends distally from a distal end 208 of a proximal shaft 202 along the entire length of a sheath 216. In this arrangement, coiled portion 214 provides reinforcement of sheath 216, such that the integrity of a sheath lumen 218 can be maintained during delivery and/or recovery of a filter or other medical device. At a distal end 222 of sheath 216, coiled portion 214 may include a closed coil or ring 234 for added stability around the distal opening of sheath lumen 218. Also see FIG. 1. Ring 234 may include a radiopaque material as a fluoroscopic aid in the placement of the sheath within a body lumen. In the embodiment of FIG. 2, a core wire shaft portion 212 includes a taper 211 to ease the transition in flexibility between the stiffer proximal shaft and the more flexible sheath portion of sheath catheter 200. A guidewire exit 224 is disposed adjacent a proximal end 220 of sheath 216.

In FIG. 3, a sheath catheter 300 according to an embodiment of the present invention includes a core wire 310 having coiled portion 314 with windings that extend proximally and distally of a distal end 308 of a proximal shaft 302. As discussed above, the distal windings of coiled portion 314 are at least partially embedded within the wall of sheath 316. In addition, the proximal windings of coiled portion 314 and a shaft portion 312 of core wire 310 are contained within a central lumen 304 of proximal shaft 302. In this manner, core wire 310 eases the transition in flexibility between the stiffer proximal shaft and the more flexible sheath portion of sheath catheter 300. Preferably, proximal shaft 302 is comprised of a hypotube. In another embodiment, the proximal shaft (not shown) is formed from a relatively stiff polymeric material, such as polyimide, with the proximal windings of core wire coiled portion 314 at least partially embedded therein. A guidewire exit 324 is substantially centrally positioned along sheath 316, between windings of coiled portion 314, to provide access to a central lumen 318.

A method of using a sheath catheter according to the present invention is described as follows. It should be understood that in the example described below, the sheath catheter is used to aid in the retrieval of a filter guidewire and that the utility of the sheath catheter is not so limited. A filter guidewire with a filter in its collapsed configuration is advanced into the patient's vasculature until the filter is beyond the intended treatment site. The filter is expanded in accordance with any mechanisms known in the art, including those mechanisms disclosed in U.S. Pat. Nos. 6,706,055, 6,818,006 and 6,866,677 previously incorporated by reference. With the filter deployed into contact with a vessel wall, one or more therapeutic catheters are advanced over the filter guidewire to the treatment site, and therapy, such as balloon angioplasty with placement of a stent is performed. Accordingly, any embolic debris generated during the therapy is captured in the filter. After the therapy is completed, the therapeutic catheter is withdrawn.

In order to prevent any difficulty in the removal of the embolic filter through the patient's vasculature, and particularly through the just placed stent, a sheath catheter in accordance with the present invention is preferably utilized. The sheath catheter is loaded onto the filter guidewire and tracked over the filter guidewire to the treatment site until a radiopaque marker on the sheath's distalmost end clears a distal end of the stent. In this manner, the sheath of the catheter effectively "lines" the stent. The filter, along with collected embolic debris contained therein, is then at least partially collapsed and pulled within the sheath. The sheath catheter and embolic filter guidewire are then removed from the patient's vasculature together. In this manner, the sheath allows the collapsed filter to be withdrawn from the patient's vasculature without incident. In another method in accordance with the present invention, the filter in an uncollapsed state is pulled within the sheath catheter to be removed therewith.

While various embodiments of the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. An embolic filter recovery catheter comprising:
an elongate tubular proximal shaft having a central lumen extending from a proximal end to a distal end thereof;
a solid core wire having a straight, uncoiled shaft portion that extends within the central lumen of the tubular proximal shaft and a coiled portion that extends from the distal end of the tubular proximal shaft; and
a recovery sheath having a proximal end attached to the distal end of the tubular proximal shaft and having a sheath lumen, wherein the coiled portion of the core wire is at least partially embedded in a wall of the recovery sheath to be fixed therein and an open distal end of the sheath lumen is sized to receive an embolic filter therethrough.

2. The catheter of claim 1, wherein the tubular proximal shaft further comprises a hypotube.

3. The catheter of claim 2, wherein the straight, uncoiled shaft portion of the core wire extends within substantially the full length of the central lumen of the hypotube.

4. The catheter of claim 1, wherein the coiled portion is fully encased within the wall of the recovery sheath.

5. The catheter of claim 1, wherein the core wire is tapered.

6. The catheter of claim 5, wherein the coiled portion of the core wire is tapered.

7. The catheter of claim 5, wherein the straight, uncoiled shaft portion of the core wire is tapered.

8. The catheter of claim 1, wherein the recovery sheath further comprises a guidewire exit disposed through the wall of the recovery sheath adjacent to the proximal end of the sheath lumen to permit a guidewire to traverse the guidewire exit when the catheter is advanced within a body lumen.

9. The catheter of claim 8, wherein the guidewire exit is positioned proximal of the coiled portion of the core wire.

10. The catheter of claim 8, wherein the guidewire exit is positioned between windings of the coiled portion of the core wire.

11. The catheter of claim 1, wherein an outer diameter of the recovery sheath is greater than an outer diameter of the tubular proximal shaft.

12. The catheter of claim 1, wherein the sheath lumen of the recovery sheath has a diameter that is greater than a diameter of the central lumen of the tubular proximal shaft.

13. The catheter of claim 1, wherein the coiled portion of the core wire has windings that extend substantially from the proximal end to the distal end of the recovery sheath.

14. The catheter of claim 13, wherein a distalmost winding of the coiled portion comprises a closed ring.

15. The catheter of claim 1, wherein the coiled portion of the core wire has windings that are uniformly spaced.

16. The catheter of claim 1, wherein the coiled portion of the core wire has windings that have a pitch that varies from a proximal end to a distal end thereof.

17. The catheter of claim 1, wherein the coiled portion of the core wire has windings that have a pitch that increases from a proximal end to a distal end thereof.

18. A sheath catheter comprising:
   an elongate proximal shaft including a hypotube having a central lumen extending from a proximal end to a distal end thereof;
   a solid core wire having a straight, uncoiled shaft portion that extends within substantially the full length of the central lumen of the hypotube and a coiled portion that extends from the distal end of the hypotube; and
   a sheath having a proximal end attached to the distal end of the proximal shaft and having a sheath lumen with an open distal end, wherein the coiled portion of the core wire is at least partially embedded in a wall of the sheath to be fixed therein and the sheath includes a guidewire exit through a side wall thereof for accessing the sheath lumen, wherein the guidewire exit is positioned proximal of the open distal end of the sheath.

19. The catheter of claim 18, further comprising a guidewire being slidably disposed within the sheath lumen such that the guidewire traverses the guidewire exit when the catheter is advanced or retracted thereover within a body lumen.

20. The catheter of claim 19, wherein a filter is attached at a distal end of the guidewire and the sheath lumen is sized to receive at least a portion of the filter therein.

* * * * *